United States Patent [19]

Alvarez

[11] 4,251,726
[45] Feb. 17, 1981

[54] DEUTERIUM TAGGED ARTICLES SUCH AS EXPLOSIVES AND METHOD FOR DETECTION THEREOF

[76] Inventor: Luis W. Alvarez, 131 Southampton Ave., Berkeley, Calif. 94707

[21] Appl. No.: 15,499

[22] Filed: Feb. 26, 1979

[51] Int. Cl.² ............................................. G09K 3/00
[52] U.S. Cl. .................................. 250/302; 250/303; 250/358 R
[58] Field of Search .............. 250/302, 303, 358, 359, 250/499, 500

[56] References Cited

U.S. PATENT DOCUMENTS

| | | | |
|---|---|---|---|
| 3,087,064 | 4/1963 | Curtice et al. | 250/303 |
| 3,146,349 | 8/1964 | Jordan | 250/303 |
| 3,809,898 | 5/1974 | Fries | 250/303 |

*Primary Examiner*—Harold A. Dixon
*Attorney, Agent, or Firm*—Townsend and Townsend

[57] ABSTRACT

Deuterium tagging in an amount at least ten (10) times the natural abundance of the deuterium isotope occurrence is disclosed. A composition of matter, including the group consisting of hydrogen containing compounds having at least one atom which is not oxygen and at least about ten (10) times the naturally occurring deuterium is disclosed. Preferred use is set forth in tagging explosives. A method of detecting the tagged article, such as explosives concealed in airline luggage includes subjecting tagged compounds with energy quanta sufficient to carry out the reaction $$D \rightarrow n + p - 2.23 \text{ MeV}$$

and detecting the number of neutrons generated is disclosed where n is a neutron, p is a proton and 2.23 MeV is the threshold energy required for the reaction. The apparatus, including a conveyor and a vertically scanning shutter is disclosed in combination with a linear accelerator for generating the X-ray energy in the order of 4 MeV and a boron triflouride proportional counter for detecting neutrons. Specific limitations are disclosed which readily adapt the method of tagged article detection to tagged explosives in airline luggage.

20 Claims, 2 Drawing Figures

FIG._2.

DEUTERIUM TAGGED ARTICLES SUCH AS EXPLOSIVES AND METHOD FOR DETECTION THEREOF

BACKGROUND OF THE INVENTION

This invention relates to deuterium tagging of compounds. A composition of matter consisting of the tagged article is disclosed. Additionally, a method of detection as well as apparatus for detecting is set forth. Preferred use of the invention is set forth in detecting the presence of explosives before they are detonated.

SUMMARY OF THE PRIOR ART

I have previously suggested and it is prior art to this disclosure to tag explosives with barium salts and detect presence of such salts by my X-ray technique as described in Alvarez U.S. Pat. No. 3,114,832 issued Dec. 17, 1963.

This patent refers to examining objects on a moving belt, to see if they contain the element for which the system is sensitive. In the case of Barium, this element is (1) inexpensive, (2) heavy enough so that X-rays responsive to its K-edge can penetrate the baggage easily, and (3) rare enough in ordinary commerce to give relatively few false alarms.

My prior art Barium tagging technique has two disadvantages. First, the Barium used as the tag always serves as a diluent. That is to say that the explosive is less effective after tagging.

Secondly, a nominal amount of shielding—such as that provided by a so called "pipe bomb"—will render this technique ineffective.

Neutron absorption in $^{14}N$, plus the subsequent "prompt" emission of a 10.8 MeV gamma has been proposed as an "untagged method" for locating explosives, as a means of finding Nitrogen in baggage. The method has three serious drawbacks. (1) Iron gives rise to a 7.8 MeV gamma ray, when it captures a neutron, and there is no practical way to distinguish the two gamma rays (7.8 and 10.8 MeV) from each other. (2) Sweaters (made of Orlon, Nylon, or wool) contained large percentages of Nitrogen, and could give false alarms, as could leather shoes. (3) There is concern that regulation by government agencies may prevent the neutron irradiation of the bags because the contents are rendered still measurably radioactive an hour after the irradiation.

Another suggested "physical method" to detect untagged explosives is based on radio frequency techniques such as nuclear magnetic resonance or nuclear quadruple resonance. These methods can be quite specific, but they suffer the very serious handicap that if the explosives are wrapped in a thin layer of aluminum foil, the radio waves are "shielded out", so the technique fails.

Considering "chemical methods" of detecting untagged explosives, the best known sensor for some kinds of explosives is the dog. Dogs can smell the vapors from dynamites and other explosives with appreciable vapor pressures, but important explosives such as RDX and PETN can't be detected by dogs. It has been proposed that if explosives were tagged by vapors that were easily detectable by instruments such as gas chromatographs—using electron attachment detectors—that the detection taggant problem would be well in hand. Much work has been done on microencapsulated liquids of the fluorocarbon family, which give off easily detectable vapors at a nearly constant rate for several years. Unfortunately, vapor taggants are easy to foil, by sealing the package with some kind of wax or glue. Knowledge of this deficiency would inevitably reach potential bombers long before the system could be implemented.

A tagging of electric detonators has been given much thought, because detonators must be used to set off high explosives. (Low explosives, such as the gun powder or smokeless powders used most frequently in "pipe bombs", can be set off by less violent triggering devices.) The vapor taggants for electric detonators are again the favored method for detection tagging of such devices. But a pipe bomb sealed as a plumber would seal it does not emit any vapors. Warned potential bombers can coat their detonators with a thin plastic layer that will hold in the vapors. For these reasons, chemical taggants are relatively easy to foil.

SUMMARY OF THE INVENTION

Deuterium tagging in an amount at least ten (10) times the natural abundance of the deuterium isotope occurrence is disclosed. A composition of matter, including the group consisting of hydrogen containing compounds having at least one atom which is not oxygen and at least about ten (10) times the naturally occurring deuterium is disclosed. Preferred use is set forth in tagging explosives. A method of detecting the tagged article, such as explosives concealed in airline luggage includes subjecting tagged compounds with energy guanta sufficient to carry out the reaction $$D \rightarrow n + p - 2.23 \text{ MeV}$$

and detecting the number of neutrons generated is disclosed where n is a neutron, p is a proton and 2.23 MeV is the threshold energy required for the reaction. The apparatus, including a conveyor and a vertically scanning shutter is disclosed in combination with a linear accelerator for generating the X-ray energy in the order of 4 MeV and a boron triflouride proportional counter for detecting neutrons. Specific limitations are disclosed which readily adapt the method of tagged article detection to tagged explosives in airline luggage.

OTHER OBJECTS AND ADVANTAGES OF THE INVENTION

An object of this invention is to disclose the use of deuterium in above natural levels as a taggant. Specifically, a novel composition of matter is disclosed. The matter includes the group consisting of hydrogen and contains compounds having at least one atom which is not oxygen with at least ten (10) times the amount of naturally occurring deuterium being present. The deuterium is present in hydrogen and nonhydrogen containing compositions and mixtures thereof.

An advantage of the disclosed composition of matter is that with a deuterium taggant, the tagged material can have precisely identical chemical characteristics as the hydrogen containing compounds. For example, in the case of a hydrogen containing tagged explosive, there is no diluent present to reduce the force of the blast.

A further object of this invention includes a method of detecting deuterium tagged articles, including exposing the article to energy quanta sufficient to carry out the reaction $$D \rightarrow n + p - 2.23 \text{ MeV}$$

and thereafter detecting the number of neutrons generated.

An advantage of the disclosed method is that concealed tagged articles may be rapidly scanned from streams of moving articles, such as uninspected luggage for stowage on airplanes. Assuming that explosives of commercial manufacturers are required to be tagged, concealment is all but eliminated.

An advantage of the disclosed tagging is that large areas may be easily searched for location of the tagged articles. A building or a plane may be evacuated and thereafter remotely inspected by X-ray. Tagged articles can be located.

A further advantage of the disclosed method is that it adapts itself readily to the pulse output of commercially available linear accelerators. Specifically, by pulsing interrogating X-ray, detectors may be correspondingly pulsed to avoid being rendered inoperative by particle "pile-up".

An advantage of the pulse interrogation includes the fact that the detector is pulsed for discrete peroids of time. In such pulsation, background slow neutron emission from natural causes—such as the natural decay of U238—and cosmic radiation is reduced in cumulative effect upon the disclosed detection process so that it may be effectively ignored.

These and other advantages will become more apparent after referring to the following specifications and attached drawings in which:

DESCRIPTION OF THE PREFERRED EMBODIMENTS

The taggant used is deuterium. Deuterium is an ideal taggant because it can be substituted for the hydrogen normally present (such a hydrogen naturally present in an explosive), rather than added as an inert dilutant. For example, the cost of the necessary deuterium to be used in the manufacture of each "explosive unit", such as a dynamite stick, is in the order of ten cents per stick.

Deuterium is certainly one of the very few substances that cannot be considered a hazard—a hundred and seventy pound man contains about 2.4 grams of deuterium. In the present invention, the deuterium content of the substance tagged (for example explosives) is enriched by a factor of above ten (10) and about twenty (20), compared to the factor of about 6900 that would make them completely deuterated. In the case of a 580 gram dynamite stick containing about 0.34 grams of deuterium—(0.06%)—the deuterium content is equal to that of 1.68 cc's of pure heavy water. It is important to reiterate that the proposed taggant is most benign, both in its effect on human beings, and in its effect on the explosive qualities of the tagged materials.

Regarding the levels of deuteration here disclosed, it is sufficient for the practice of this invention if ten (10) times or more above the level of naturally occurring deuterium is utilized. Levels of fifteen (15) times or more are preferred. For certain application where "false alarms" are to be avoided, concentration twenty (20) times and above the naturally occurring level may be desired.

PHYSICS OF THE METHOD

The method proposed is based on several physical phenomena. The first is that of all the 100-plus known chemical elements, with their approximately 1000 different known isotopes, $^9$Be and deuterium have the lowest energy thresholds for the nuclear reaction in which a photon is absorbed, and a neutron is immediately emitted. In nuclear physics, this is called the ($\gamma$, n) reaction, where $\gamma$ means a $\gamma$-ray (or X-ray), and n means a neutron. $E_{th}$, the threshold energy, is 1.67 MeV for $^9$Be (the only stable Be isotope). The next lowest value of $E_{th}$ is the 2.23 MeV for deuterium, the hydrogen isotope of mass 2. For all the 1000 other isotopes, the value of $E_{th}$ is higher; the average value is near 8 MeV. (There are 4 exceptions which exceptions are of no practical interest, because the 4 other isotopes with values of $E_{th}$ below 2.23 MeV all have halflives less than 15 seconds, and they are therefore never seen outside a physics laboratory or a nuclear reactor installation; these exceptions are:

$^{11}$Be, with a halflife of 13.7 sec, $E_{th}=0.5$ MeV,
$^{15}$C, with a halflife of 2 sec, $E_{th}=1.21$ MeV,
$^8$L, with a halflife of 0.8 sec, $E_{th}=2.03$ MeV,
$^6$He, with a halflife of 0.8 sec, $E_{th}=1.92$ MeV,)

Beryllium, in some inert form, could be used as a taggant. However, modern regulatory practice concerning the hazards of Beryllium and all its compounds, presents prohibitive constraints.

Discarding Beryllium, deuterium proves particularly advantageous. The next hghest threshold energy for neutron production is for $^{17}$O, at 4.14 MeV; the concentration of $^{17}$O in ordinary oxygen is one part in 2700. Therefore, X-ray energies somewhat above 4.14 MeV can be used. However, care must be taken to avoid the next enery threshold, which is for $^{13}$C, at 4.95 MeV. $^{13}$C exists as one part in 90, in all carbon. If the 4.95 MeV energy level is exceeded by very much, too many neutrons will appear from all organic matter. Neutrons from the added deuterium that forms the basis of the method would then be obscured.

In the preferred example of tagging, explosives in luggage bags, it will be noted that Beryllium will not cause any appreciable number of false alarms. Two items are of importance: (1) the ($\gamma,\eta$) cross section for Be starts to become appreciable before that of D. However, over the X-ray spectrum from a 4 MeV X-ray source, the effective nuclear cross section per Be atom is about $\frac{1}{3}$ of that per D atom, so the cross section per gram is down by more than a factor of twelve. Therefore, in order to give the same number of neutrons as a single stick of dynamite, the mass of Be would have to be 12 times that of the 0.34 grams of D, or 4 grams of Be.

4 grams of Be is a most unusual amount of Be to find in a bag, where the only appreciable sources of Be are beryllium copper springs and the mineral beryl (emerald or aquamarine). Be-Cu alloys contain 2% of Be, so 4 grams of Be would indicate the presence of 200 grams of Be-Cu springs. 4 grams of Be could also be found in 80 grams of emerald or aquamarine. These two suggested false alarm scenarios are most unlikely, as to airline luggage bags, but very easy to distinguish from the excess deuterium being searched for. Further, dropping the X-ray energy down to 2.2 MeV, and reexamining for tagged articles in a luggage bag, one can tell immediately that the extra neutrons come from Be, and the bag can be certified as safe. This situation will arise so seldom that I consider this to be an acceptable solution to the Be "problem".

I therefore, assume that we will scan all baggage on a moving belt, with the X-ray beam from a 4+ MeV linear accelerator. Varian Associates of Palo Alto manufactures as a commercial item of manufacture such an X-ray machine, with the following characteristics:

| Varian Associates Model 400 Linac | |
|---|---|
| Rated x-ray output (r/min at 1 m unflattened) | 400 |
| Beam energy (nominal MeV) | 4 |
| Focal spot size (mm diameter) | 2 |
| Beam current (peak mA) | 160 |
| Target material (Thickness approximately 1 electron range) | tungsten |
| Approximate accelerator guide length (meters) | 0.3 |
| Pulse repetition frequency | variable 80–320 |
| Approximate pulse length (μsec) | 3.9 |
| Approximate maximum duty factor | 0.0012 |
| Approximate maximum beam power (Watts) | 750 |
| Microwave power source | magnetron 2 MW peak 2998 MHz |

I use an electron linear accelerator as my source of X-rays. If the maximum energy of the electrons is 4 MeV, X-rays of all energies up to 4.00 MeV will be generated, and no neutrons can be made, except when such X-rays bombard hydrogen, with its small admixture of deuterium, and its 2.23 MeV $E_{th}$. It will be assumed fron now on that any observed neutrons come from the $(\gamma, \eta)$ reaction on deuterium; the Be problem has already been addressed.

It turns out that the Varian model 400 linear accelerator is almost ideally suited to the detection of slightly deuterated explosives in luggage. An improved X-ray generator could result where the pulse rate changes from 320 Hz to 1000 Hz, and pulse length drops from 3.9 μsec to 1.3 μsec. This will keep its average power the same, but allow smaller "pixels" (picture elements) in search. Such modification can be made by those having ordinary skill in the art. Hereafter, the assumption of 1000 Hz and 1.3 μsec. will be used.

Using the case of belt transported luggage, belt speed of 1 meter per second will be assumed. At that rate, one can examine close to 4000 bags per hour, with one station. If we assume that the average plane has 250 checked bags—many passengers never check any bags—then one station can process all the bags located onto 16 planes per hour, or one plane every 3.75 minutes on the average. Calculations confirm that the 1 meter per second belt speed is a reasonable match with modern air traffic rates.

Figure 1:
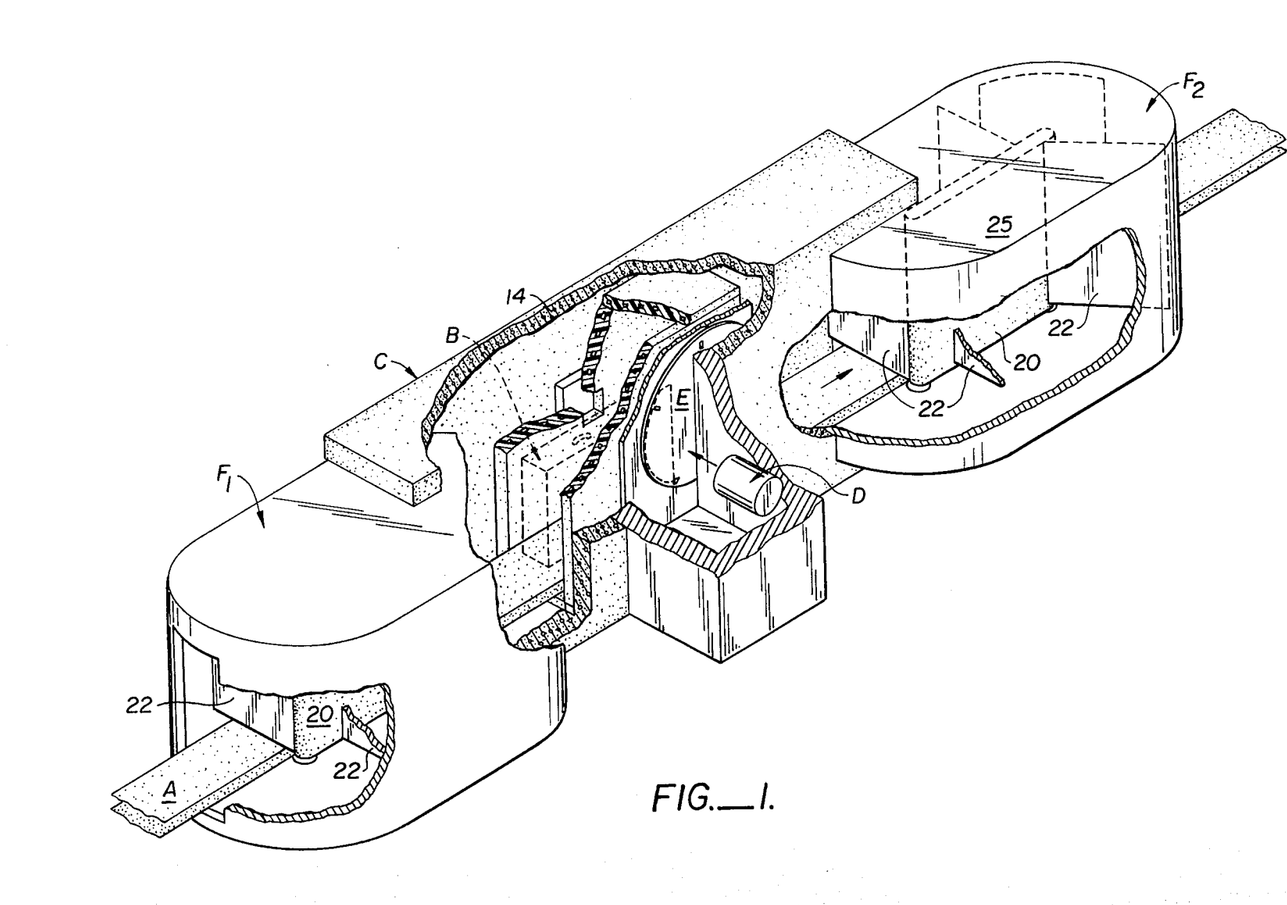
FIG. 1 is a perspective view of an apparatus for interrogating a stream of airliner bound luggage. The photographs schematically showing a linear accelerator of commercial manufacturer scanning through a shutter the stream of luggage; and, FIG. 2 is a side elevation view along the lines hereto of FIG. 1 of a shutter that can be utilized with this invention.

Referring to FIG. 1, a continuous luggage conveyor A is shown for conveying discrete articles of luggage B across an inspection station C of this invention. Linear accelerator D in combination with a shutter mechanism E for defining the pixels of this invention is illustrated. As is common in the X-ray examination arts, paired shielding doors $F_1$ and $F_2$ are illustrated.

Conveyor A is a single and continuous luggage conveyor. It extends the full length of the luggage inspection station and operates at a conventional speed in the range of 1 meter per second.

Luggage B is included to be any standard article permitted on airlines. Such articles can include conventional suitcases, such as the one illustrated. It will be understood that while illustrative dimensions and dimension limitations are given here, other dimension limitations, such as those required by other aircraft limitations outside the United States, may as well be used.

Inspection station C is shielded to avoid the inadvertent emission of X-ray. Such shielding includes conventional concrete end wall 14 as well as lead 16 surrounding accelerator D.

Sealing either ends of the chamber C there are revolving doors. These respective revolving doors are here shown attached to an endless belt conveyor between respective paired axles (not shown). Each of the endless belt conveyors has protruding normally substantially therefrom a plurality of doors 22. As is known, these doors sweep an oval path upon a complete revolution of the endless belt.

Doors 22 are contained within a housing 25 constructed of shielded material. Housing 25 includes an overall inside height equal to the heighth of the door and an overall oval width coincident to the path of the radially remote edge of the doors 22.

Operation of the respective doors 22 and their housing 25 is readily understood. A revolving door has the property that it always remains closed. That is to say there is always one or more doors in between an entrance portal and an exit portal to such doors. Realizing that the respective conveyors A penetrate the revolving doors each of the revolving door mechanisms $F_1$, $F_2$ at respective entrance and exit portals for each door will be realized that radiation cannot exit the tunnel without "seeing" and being blocked by one of the doors.

Figure 2:
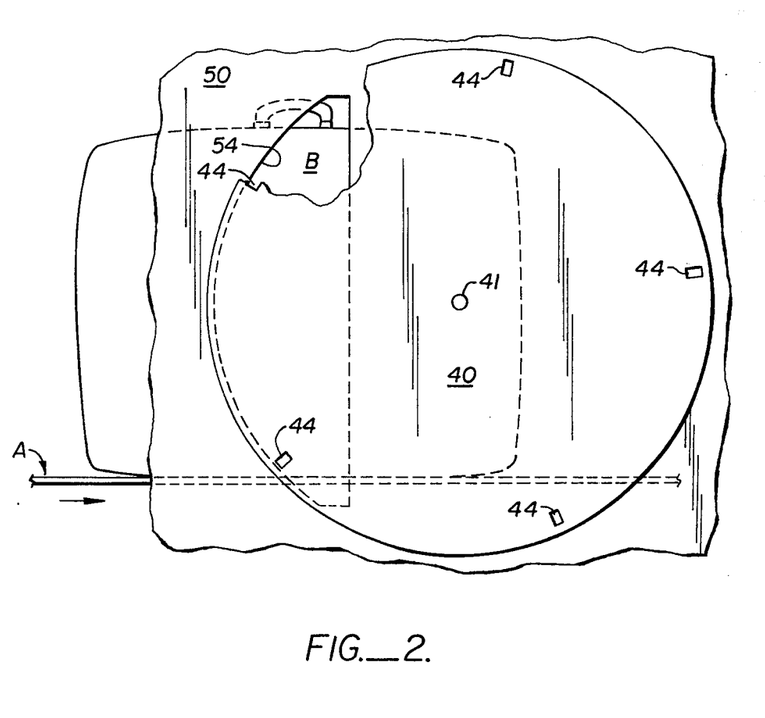

Having set forth the general construction of the station, the function of the linear accelerator D and the shutter mechanism E can now be set forth with respect to FIG. 2.

The linear accelerator is pulsed and addressed to revolving lead shutter wheel 40 rotatable about an axis 41. Wheel 40 defines in its periphery 5 pixel openings 44. These respective pixel openings in turn sweep from top to bottom passing luggage B.

Underlying the wheel 40, there is a conventional lead shield 50. Lead shield 50 defines therein an arcuate opening 54. It will be seen that the pixel openings 44 when registered over opening 54 define a progressive path for pixels to pass.

It will be remembered that the accelerator of this invention is pulsed. Pulse times are specifically selected so that each pixel permits the entrance of X-ray of the sequential overlying pixel areas.

It will be appreciated that the particular shutter mechanism herein illustrated is in effect sweeping the luggage in the Y-direction while conveyance occurs in the X-direction. This being the case, it will be realized that any number of mechanisms for providing sweep may be sufficient in the practice of this invention. Moreover, the rates of sweep and number of pixels utilized may be adjusted by those having ordinary skill in the art in accordance with the parameters of the search desired.

A benefit is gained from the pulsed nature of the X-ray source—either 3.9 or 1.2 μsec long. But if it were not for that pulsed property of the beam, we would have to count the neutrons while the intense X-ray beam was "turned on". Such a "continuous mode" of operation is possible at low X-ray beam intensities. However, the design of such a device to work when we have only 1 to 3 milliseconds to complete the analysis of the neutron counting rate from each pixel would be difficult. The basic problem is that any counter that is sensitive to a small number of neutrons will also be sensitive to "pile-up", when exposed to a very intense flux of high energy X-rays.

Fortunately, in the pulsed mode, we can make use of the fact that in order to count neutrons with high efficiency, it is first necessary to slow them from the "MeV energy range" in which they are created, down to the "thermal energy range", in which $^{10}B$ has an exceptionally large interaction cross section—3800 barns=$3.8 \times 10^{-21}$ cm$^2$. The time for the high energy neutrons to cover even several meters is less than 1 $\mu$sec. The time for the neutrons to be slowed down (in hydrogenous materials) to thermal neutrons is also of the order of, or less than, 1 $\mu$sec. But the time that the neutrons can "live", (and "diffuse"), as thermal neutrons in hydrogenous materials, is measured in tens of microseconds. This latter fact is of the greatest possible importance to the proposed method; we generate the neutrons in an intense burst of X-rays, which "paralyzes" the BF$_3$ proportional counters. But the counters recover in a microsecond or so, and are therefore able to detect the high energy reaction products of the $^{10}B$ + slow neutron reaction, in a benign environment, in which no X-rays are being generated. The important reaction in the $^{10}BF_3$ gas that fills the counters—which are in turn embedded in the hydrogenous "moderating material"—is the following:

$$n + {}^{10}B \rightarrow {}^{4}He + {}^{7}Li + 2.30 \text{ MeV}$$

The cross section for this reaction increases inversely with the velocity of the neutron, which is the reason for slowing the neutrons down to their thermal velocity of $2.2 + 10^5$ cm/sec, at which velocity, the cross section has the very large value mentioned above.

As FIG. 1 shows, it is preferred that lead shielding would be used on the "linac side" of the station, and concrete on the far side. The thickness of concrete required is between 2 and 3 meters, and the lead is about 1 foot thick. It is generally necessary to protect personnel from X-rays "scattered out the tunnel", but that is a problem that is known and solved in the "carry-on baggage" X-ray units at airports. Because of the Compton effect, scattered X-rays are less penetrating than the original X-rays, and they are much less intense. The solution of this problem can be to block the tunnel ends with a few inches of lead. In FIG. 1 the tunnel has incorporated the equivalent of a "revolving door". Such a door is "always closed", even though people can pass through it. Such a device would obviously solve the radiation leakage problem.

Boron triflouride counters are preferred for neutron detection. The reason that the BF$_3$ counters can be made to respond to slow neutrons, and ignore all other background radiation is that the energetic $^4$He and $^7$Li nuclei that are emitted "back to back" from neutron collision in the BF$_3$, are going slowly (compared to the velocity of light), and have charges of 2 and 3, respectively. So they ionize the BF$_3$ gas much more strongly than the electrons (from photon interactions), and the cosmic ray muons that cannot be shielded away. It will be noted that the ionization rate varies roughly as $Z^2/v^2$, where Z is the charge, and v is the velocity. So the large $Z^2$ and low $v^2$ of the $^4$He and $^7$Li permit those particles to dump all their energy in the gas, whereas electrons and muons can deposit only a few hundred kiloelectron volts—at the most—in passing through the counter. So one sets a "bias level" in the amplifier that only passes the large pulses from the neutron reaction, and rejects all other particles that traverse the detectors.

We must look at one further question in connection with the counter background, and that is, "What is the ambient neutron flux due to cosmic rays and spontaneous fission of $^{238}U$ in the ground". This flux has been measured, and it is 65 neutrons per square meter, per second, at sea level. Of these neutrons, 23 have energies below 0.4 eV (the "Cadmium cutoff"), and 42 have energies above that energy. These would be frightening numbers if we were doing our neutron counting on a continuous basis, since we will be using detectors with an area of an appreciable fraction of a square meter, and we are looking for neutron counts of the order of 100 per second from one stick of dynamite. But again, the pulsed nature of the detectors comes to our rescue. The time between pulses (at the 1000 Hz pulse rate) is about 1000 $\mu$sec, so if we count neutrons for only the 30 $\mu$sec after our X-ray pulse, we cut our background flux by a factor of 33, to 1.8 neutrons per square meter per second, and if we have a detection efficiency of 0.2, we will detect background neutrons at the rate of about 1 per 3 bags. Remembering the configuration of FIG. 1, the concrete shielding will also lower the background neutron level. Had we been in trouble from this background, we could have added some boron shielding around the whole detector assembly. But fortunately, this is not necessary to the practice of this invention. The few neutrons that are freed when D or Be is hit by X-rays will cause no measurable radioactivity—those neutrons are such a negligible fraction of the "background neutrons" to which the bag is always exposed, that there is no way in which any nuclear physicist, with access to the most sensitive instruments, could tell whether a bag delivered to a passenger at the end of the trip had been, or had not been, exposed to the X-ray beam.

It will be realized without detailed explanation that remotely controlled detectors could examine a whole airplane from the outside—if it was suspected of having a bomb on board—or that could search a similarly suspected building. In both cases, there would be no people in the neighborhood during the X-ray bombardment, so shielding would not be required. Scanning would not be used, but instead, a large area would be sprayed with X-rays, and the large area neutron detector would have much more time to accumulate counts. In the baggage detector, one pixel is exposed for about 1 millisecond, and any neutrons from that pixel must be picked up immediately, because that area will not be irradiated with X-rays again. But in the "remotely controlled search detector", each projected area is probed for a much larger time—of the order of a second or more, so the sensitivity is much higher. In this mode, the X-rays may pass through a large neutron detector on the way to the deuterated explosives, and the neutrons will be counted as they return. There are "tricks" that can be used to speed up the recovery of BF$_3$ counters that have been "blasted" by X-rays; one can either lower the counter voltage when the X-ray pulse is on, or reverse it during that interval.

While the remotely controlled search mode is an important example of this invention, I will concentrate in this disclosure on the preferred embodiment of a baggage searching device.

In order to calculate the number of neutrons emitted from an irradiated volume of material in the bag (the "pixel"—picture element) I need to know (1) how much D that volume contained, (2) the $(\gamma,\eta)$ cross section for D as a function of photon energy, (3) the X-ray spectrum incident on that volume—relative numbers of photons as a function of energy between the 2.2 MeV threshold and the $\approx 4$ MeV upper limit, and (4) the absolute flux of X-ray photons at the bag—measured in quanta per cm² per sec.

We can control (1) by deciding what percent of the H atoms I will change to D, in the explosive material; (2) has been measured frequently, and there are theoretical curves that fit the experimental data well; (3) is treated in some detail in an excellent paper by A. Brynjolfsson and T. G. Martin, in the International Journal of Applied Radiation and Isotopes, 22, 29–40 (1971); (see prticularly their FIGS. 5 and 6); and (4) the determination of the absolute flux, is the least well known of the four required bits of data. I have calculated it in two quite different ways, and they agree to better than a factor of two—I will use the lower of my two estimates, to be conservative.

The first method used the tables and the figures in the 1971 paper, together with Varian's tabulated beam current of 160 ma. I could then calculate the total number of "useful photons" (between 2.2 and 4.0 MeV) emitted per second. But the paper does not give a good number for the ratio of the "forward flux" to the average flux. "Forward enhancement" may be inaccurate.

Method number 2 starts from the "Rated X-ray output", which Varian tabulates for the Model 400. This number is 400 rads/minute at 1 meter from the X-ray target ("straight ahead") when the "field flattener" is not in place. (The flattener perferentially absorbs some of the X-rays that would go straight forward, and thereby makes the forward peak less pronounced.)

We can calculate the power density in the forward X-ray beam (watts/cm²) from the number of rads per second, and the absorption coefficient of the X-rays in water. Recall that an X-ray exposure of 1 rad is defined to be the deposition of 100 ergs in each gram of material. The entities that deposit the energy are the secondary electrons that are knocked out of the material under the influence of the X-rays. So if we have a beam of X-rays that transports P watts/cm² through a surface, and goes on the average, a distance d cm before it is totally absorbed, then it dumps, on the average, 1/d of its power into each of the first cubic centimeters of the material. And if we assume the material is H₂O, we can use cc's and grams interchangeably. If we remember that 1 watt is 1 joule per sec; 1 joule is 10⁷ ergs; and 1 rad (r) is 100 ergs per gram, it is simple arithmetic to calculate that the radiation dose (in rads per sec) is $$\text{Dose rate} = \frac{10^7 p}{100 d} \, r \text{ per sec.}$$

(In my calculations from here on, I will usually give numbers to 2 or 3 significant figures, even when I say that I only know some parameter to 10%. Of course, the best solution seems to be to quote intermediate results to 3 figures, but eventually not to believe the final results to better than 10%).

We can look up d in tables of X-ray absorption, and we find that it varies from 46 cm (at 4 MeV) to 30 cm (its maximum value at 0.5 MeV) back to 46 cm (at 90 KeV—which, for this purpose, can be considered to be the lower limit of the spectrum. The appropriate value of d to use is between 30 and 40 cm. 37 cm is very probably within 10% of the correct value, and I will use that value from here on.

The tabulated dose rate is 400 r/min=6.67 r/sec. Therefore the X-ray power density is $$P = \frac{6.67 \times 37}{10^5} = 2.47 \times 10^{-3} \text{ watts/cm}^2$$

We now want to convert this power density to a flux of useful X-ray photons. We can assume, in order to simplify matters, that all the useful photons have their average energy 3.1 MeV—(4.0+2.2)/2. A numerical integration of the curves of the 1971 X-ray article, shows that 29% of the X-ray power was in the "useful region" between 2.2 and 4.0 MeV. So the "useful X-ray power density" is $2.47\times10^{-3}\times0.29=7.16\times10^{-4}$ watts/cm²

We can now make the conversion to the photon flux at one meter, by remembering that 1 electron volt is $1.6\times10^{-19}$ joules. Therefore, a 3.1 MeV photon has an energy of $3.1\times10^6\times1.6\times10^{-19}=4.96\times10^{-13}$ joules. The photon flux is then (at 1 meter)

$$\text{Flux}=7.16\times10^{-4}/4.96\times10^{-13}=1.44\times10^9 \text{ sec}^{-1}$$

I will arbitrarily assume that the X-ray source will be two feet (60 cm) from the center line of the belt, so the useful flux of photons at the distance will be $$\text{Flux} = \left(\frac{39.37}{24}\right)^2 \times 1.44 \times 10^9 = 3.87 \times 10^9 \text{ cm}^{-2} \text{sec}^{-1}$$

Analysis of the variation of flux from the center of the bag to its top or bottom is useful. Since the distance from the X-ray target to the center of the bag is arbitrarily set at 24″, and the FAA current maximum allowed height of a bag is 24″ (together with a maximum length of 30″, and a maximum thickness of 14″), the maximum angle at which X-rays must strike the top or bottom of the bag is $\tan^{-1} 0.5=26.6^0$. According to the 1971 article, the flux from a 4 MeV X-ray tube drops to 0.45 of its central value at $\pm 26.6^0$. But the solid angle for detection of neutrons increases toward the top and bottom of the bag, so the effective neutron counting rate per unit of deuterium probably does not drop to less than 75% of its "central value". Dropping the assumed flux from its central value, just calculated, of $3.87\times10^9$ cm⁻²sec⁻¹ to 0.85 of that value, or $3.3\times10^9$ cm⁻²sec⁻¹, can account for bag flux variation.

The number of nuclear reactions taking place (anywhere, in any process) can always be expressed as (1) a flux, times (2) a cross section, times (3) a number of atoms with that cross section, times (4) the time interval. One often multiplies (2) and (3) to get what is called the "macroscopic cross section". Then the reaction rate is the flux times that macroscopic cross section.

According to the literature, the $(\gamma,\eta)$ cross section on D increases rapidly from 0, at the 2.2 MeV energetic threshold, to $1.0\times10^{-27}$ cm² at 2.5 MeV. It rises to $1.5\times10^{-27}$ cm² at 2.76 MeV, and to $2.5\times10^{-27}$ cm² at 4 MeV. I think that a resonable average to take over the spectrum of useful X-rays is $2.0\times10^{-27}$ cm².

To obtain some feeling for the neutron production in a typical stick of dynamite, assume that we have a 2" diameter×8" long stick of DuPont Power Primer$^R$ dynamite, weighing 560 grams. Power Primer being a registered trademark of the IE DuPont corporation of Wilmington, Del. If this stick has its deuterium content raised to the equivalent of 560 grams of "20 times enriched heavy water", it will contain the equivalent of $560 \times 20/6900 = 1.62$ gms of $D_2O$, or $2.90 \times 10^{-3} \times 4/20 = 3.25 \times 10^{-1}$ gms of D. Since the atomic weight of D is 2, this amount of deuterium contains $(3.25 \times 10^{-1}/2) \times 6 \times 10^{23}$ atoms.

$N_D = 9.84 \times 10^{22}$ D atoms

The area of the dynamite stick is $2 \times 8 = 16$ sq. in., so the average number of atoms "behind" each one (1) square inch pixel is $$N_{pix} = \frac{9.84 \times 10^{22}}{16} = 6.15 \times 10^{21}$$

If we multiply $N_{pix}$ by $\sigma(\gamma,\eta)$, we obtain the average macroscopic cross section per pixel $$\Sigma = N_{pix} \times \sigma = 6.15 \times 10^{21} \times 2 \times 10^{-27} = 1.23 \times 10^{-5}$$
$$cm^2$$

This mascroscopic cross section, compared to the cross section of a pixel ($2.54 \times 2.54 = 6.45$ cm$^2$), can be considered to be the "opacity of the pixel". As an example, if the mascroscopic cross section were 0.645 cm$^2$, then one tenth of the X-ray photons would interact to make neutrons. But since $1.23 \times 10^{-5}$ cm$^2$ is only $1.91 \times 10^{-6}$ of the area of the pixel, the chance that a "useful X-ray photon" interacts to make a neutron is only $1.91 \times 10^{-6}$.

We have one factor working for detection—the large number of X-ray photons passing through each square centimeter per second $-3.3 \times 10^9$ cm$^{-2}$sec$^{-1}$, and we have another factor working against detection—the short time each pixel is exposed to the X-ray beam. In the standard Model 400, this time can be considered to be the time between pulses, or 1/320 Hz = 3.12 msec. Reducing the pixel size to 1 square inch is helpful. This pixel size is closer to $10^{-3}$ of the area of the bag. (Since the bag can have an area of $24" \times 30" = 720$ Sq. inches, we can scan a bag in 0.720 sec—at the rate of 1000 pixels per second—and have a resonable space between bags that move by at the 40 inches (1 meter) per second rate mentioned earlier.) This allows the exposure time per pixel to be reduced to 1 msec. So the number of neutrons generated when looking at 1 square inch of one stick of enriched dynamite, for 1 millisecond is $$N_n = Flux \times \Sigma \times \Delta t = 3.3 \times 10^9 \times 1.23 \times 10^{-5} \times 10^{-3}$$
$$= 41$$

This is a useful number. Whenever the X-ray scanner passes over a single $2" \times 8"$ stick of enriched dynamite, it will generate 41 neutrons for each of the pixels covered by the dynamite stick, or $16 \times 41 = 656$ neutrons. If we count 16% of those neutrons, the total "signal", per dynamite stick, is $0.16 \times 656 = 105$ neutrons. (I have assumed in this calculation that the dynamite stick is exactly aligned with the scan, so that it is fully scanned in 16 pixels. But no matter how it is oriented, we will always count the same 105 neutrons, as the scanning disk rotates, and as the belt moves the bag. A cathode ray tube can show the stick, with the course one square inch resolution.)

We have already seen the background counting rate, from cosmic rays, etc., is essentially zero. So the 100 or so neutrons gives a very large signal compared to the natural background.

We must now compare this number of neutrons with the number that would be generated in a column of ordinary hydrogenous material that had the maximum allowed thickness (along the beam direction) of 14 inches. This is fortunately a simple calculation, and, in fact, it is what really sets the level of enrichment that I have suggested to be "20×".

We simply ask the question, "How thick would a mass of ordinary water have to be to give as many neutrons per pixel as our two inch thick, 20× enriched dynamite stick"? The answer is, to a sufficient approximation, $2" \times 20 = 40"$. In other words, the only way we can get the same macroscopic cross section of deuterium behind any pixel is to use ordinary hydrogen, with its natural D concentration, but make it 20 times as thick, to compensate for its 20 times smaller D concentration. The fact that 40" is approximately 3 times the current Federal Aviation Agency's mandated maximum bag thickness of 14" is what convinces me that false alarms can be avoided at the suggested 20× enrichment.

The detector also can be configured so that it always knows how many grams of material are behind each pixel. Actually, it measures the number of electrons per pixel, rather than the number of grams, but that is a small difference, due mainly to the fact that a gram of hydrogen has twice as many electrons as a gram of other low Z materials. Far side BF$_3$ counters can be used as ionization chambers, while the X-ray pulse is "on", to measure the Compton-scattered X-rays from each pixel. This gives us the number of electrons behind each pixel, and that information can help microprocessor software system decide how seriously to take a higher than usual neutron count that came from—say a bottle of liquor—that was 1 foot high, and oriented with its axis along the X-ray beam direction. Of course, as I have already pointed out, such a bottle can give only one-third as many neutrons as the dynamite stick.

We can get additional information about the material in the bag by monitoring the transmission of the low energy ($\approx 100$ KeV) X-rays, as is done in the standard "carry-on baggage X-ray units". This can be done by allowing a microprocessor through appropriate software to know three things: (1) how much D is behind each pixel, (2) how many electrons are behind each pixel, and (3) what the average atomic number of the material is behind each pixel.

The "third detector" would be made of relatively high atomic number, and would respond primarily to the X-rays in the 0.1 MeV range. It is my best judgement that the hardware I have suggested, plus appropriate software to be based on the known properties of X-rays of various energies, on which I have touched, will make it impossible for an enriched explosive to escape detection, and at the same time produce so few false alarms that the system will be judged to be "acceptable".

Calculation of what the average radiation does to material inside the bag can simply be made. We have assumed that our "modified Varian Model 400" will give the 400 r/minute dose rate (from which its designation was derived), but in 1000 pulses per second, rather than in the 320 pulses per second, maximum, that the Model 400 employs. So the dosage to each pixel would be $$\text{Dose} = \frac{400}{60} \times 1000 = 6.67 \text{ mrad}$$

if the target were 1 meter from the bag. But since we have assumed that the target is 24 inches (rather than 40 inches) from the bag, the actual dose is Actual Dose = $6.67 \times (40/24)^2 = 18.5$ mrad It is most probable that the 18.5 mrads exposures per bag search will be deemed acceptable to unexposed film. For purposes of comparison, see chapter on Photographic Film Dosimeters, in the Manual on Radiation Dosimetry, edited by Holm and Berry, Marcel Dekker, Inc., New York, 1970. This reference states that with film dosimeters, doses from about 1 mR to 100 mR can be measured. But in the low ranges, the films must be in contact with a fluorescent material, so it is the response of that material, rather than the film itself, that is being observed. The film that is used is standard X-ray film, which is of course made as sensitive to ionizing radiation as possible. It is probable that ordinary films, used by photographers, are considerably less sensitive to X-rays. The one curve shown in this chapter plots "net optical density" (of X-ray film) vs. "γ-ray exposure in R". For an exposure of 18 mR, the optical density is less than 0.1. (An optical density of 1 means that 10% of the light is transmitted, and an optical density of 2 means that 1% of the light is transmitted. On this log scale, a density of 0.1 means that 79% of the light is transmitted.)

Two other important items of interest that do not involve large explosive units that contain a great deal of hydrogen, such as the dynamite on which we have concentrated attention so far are detonator caps and gun powder. The first of these, the detonator cap, is typically 7 mm in diameter, and 5 cm long. We would like to put enough D in this small volume to be sure that it would stand out by giving about 25 counted neutrons in one pixel. This is four times the number from any one pixel in the "standard" stick of dynamite discussed earlier, but only one quarter of the total amount in that same stick. We can easily incorporate that amount of deuterium within the explosive material (plus the "plug", if needed), by raising the concentration of deuterium. (To recall the numbers, we used 0.34 gms of deuterium—1.68 gms equivalent of fully enriched $D_2O$ to tag the dynamite.) So it is desirable that each detonator should contain $0.34/4 = 0.085$ gms of deuterium. If this were in the form of 100% deuterated water, it would weigh $5 \times 0.085 = 0.41$ gms, and have a volume of 0.37 ccs. In view of the much larger volume of the detonator, it would seem to be reasonable to incorporate the 85 miligrams of D in the primary explosive in the detonator.

Finally, gunpowder, which contains no hydrogen, cannot have a substitute D for H in its manufacture. But in the case, we can do what all other tagging schemes propose to do—add the required deuterium in some inert compound, in the very small percentage by weight required. I think it is impressive that a pipe bomb containing a few tenths of a gram of deuterium can be detected with certainty—both the high energy X-rays and the neutrons pass through the iron pipe with very little attentuation.

What is claimed is:

1. Apparatus useful for the detection of deuterium tagged articles comprising: a source of X-ray photons sufficient in frequency and energy to cause the following reaction but having energy less than 4.14 MeV:

$$D \rightarrow n + p \text{ 2.23 MeV};$$

and a neutron detector embedded in a hydrogenous material aligned in the path of said generated neutrons to detect generated neutrons; and means for conveying said article between said photon source and neutron detector.

2. The invention of claim 1 and including means for pulsating said photon source and means coupled to said detector for pulsating said detector and means cooperatively connected between said photon source and detector to turn off said detector during photon pulsations of said source.

3. The invention of claim 1 and including means for detecting X-ray absorption due to the atomic weight of said article scanned and means for determining Compton electron scattering of said X-rays from said photon source.

4. The invention of claim 1 and including means for dropping said photon source to about 2.2 MeV to detect abundant amounts of beryllium.

5. A method of scanning a series of conveyed articles for randomly placed deuterium tagged articles comprising the steps of: an X-ray providing photon source scanning transversely through the conveyed path of said article having at least one neutron detector aligned to receive said emitted neutrons from the reaction:

$$D \rightarrow n + p - 2.23 \text{ MeV}$$

where p is a proton and n is a neutron; said photon source and neutron detector going on opposite sides of said conveyed article path; providing adjacent to said neutron detector means for generating said photons in side by side pixels; pulsating said photon source with at least one pulsation for each said pixel and activating said detector to measure neutrons when photon source is not emitting said photons.

6. The method of claim 5 and including the steps of measuring Compton X-ray scattering while proton source is emitting said protons.

7. The method of claim 6 and including the steps of measuring X-ray absorption while said proton source is emitting protons.

8. A method of detecting a deuterium tagged article comprising the steps of exposing said article to pulses of energy quanta sufficient to carry out the following reaction but less than energy quanta of about 4.14 MeV:

$$D \rightarrow n + p - 2.23 \text{ MeV}; \text{ and}$$

detecting the number of neutrons generated.

9. A method of tagging hydrogen-containing explosives comprising substituting deuterium for at least about 10 out of every 6900 hydrogen atoms.

10. A method for tagging non-hydrogen containing explosives comprising the step of adding deuterium.

11. A novel composition of matter selected from the group consisting of hydrogen containing compounds having at least one atom which is not oxygen and at least about 10 times the amount of naturally occurring deuterium and hydrogen and non-hydrogen containing compositions and mixtures thereof comprising deuterium.

12. The invention of claim 11 and wherein said composition of matter is explosive.

13. A novel composition of matter comprising hydrogen, oxygen and at least one other element, said hydrogen comprising at least about 10 times the naturally occurring amount of deuterium.

14. The invention of claim 13 and wherein said composition of matter is explosive.

15. A novel composition of matter comprising hydrogen and at least one element other than oxygen, said hydrogen comprising at least about 0.1449 percent more deuterium than would naturally be present.

16. The invention of claim 15 and wherein said composition of matter is explosive.

17. A novel composition of matter comprising hydrogen and at least one atom other than oxygen, said hydrogen comprising at least about 10 times the naturally occurring deuterium.

18. The invention of claim 17 and wherein said composition of matter is explosive.

19. A novel composition of matter comprising a hydrogen-containing explosive, said hydrogen comprising at least about 0.14 percent by weight deuterium.

20. Composition according to claim 19 wherein said explosive is a detonating cap and the deuterium about 0.28 percent by weight deuterium.

* * * * *